US009890882B2

(12) United States Patent
Zeko et al.

(10) Patent No.: US 9,890,882 B2
(45) Date of Patent: Feb. 13, 2018

(54) INTEGRATED FLUIDIC CONNECTION OF PLANAR STRUCTURES FOR SAMPLE SEPARATION DEVICES

(71) Applicant: AGILENT TECHNOLOGIES, INC., Loveland, CO (US)

(72) Inventors: Darijo Zeko, Ettlingen (DE); Manfred Berndt, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 123 days.

(21) Appl. No.: 14/771,392

(22) PCT Filed: Feb. 28, 2013

(86) PCT No.: PCT/IB2013/051604
§ 371 (c)(1),
(2) Date: Aug. 28, 2015

(87) PCT Pub. No.: WO2014/132103
PCT Pub. Date: Sep. 4, 2014

(65) Prior Publication Data
US 2016/0003383 A1   Jan. 7, 2016

(51) Int. Cl.
*B01L 3/00* (2006.01)
*F16L 21/02* (2006.01)
(Continued)

(52) U.S. Cl.
CPC .............. *F16L 21/02* (2013.01); *B01D 15/10* (2013.01); *B01D 15/14* (2013.01);
(Continued)

(58) Field of Classification Search
CPC .... B01L 3/502715; B01L 3/5027; B01L 3/50; B01L 2300/0816; B01L 2300/0809; B01L 2300/08; F16L 21/02; F16L 21/00
(Continued)

(56) References Cited

U.S. PATENT DOCUMENTS 4,982,597 A   1/1991  Berger
5,988,703 A   11/1999 Craig
(Continued)

FOREIGN PATENT DOCUMENTS

DE   102011075146   11/2012
EP         309596 A1    4/1989
(Continued)

OTHER PUBLICATIONS

Chinese Office action dated Jul. 5, 2016 from related Chinese Application No. 201380073962.3.
(Continued)

*Primary Examiner* — Christine T Mui

(57) ABSTRACT

A fluidic device includes a planar structure constituted by a plurality of laminated layers and accommodating a fluid channel extending up to a surface of the planar structure, and a female adapter piece configured for a fluid-tight accommodation of a male adapter piece having a fluid conduit. The the female adapter piece is connected or connectable with the planar structure so that, when the male adapter piece is accommodated in the female adapter piece, the fluid conduit is brought in fluid-tight fluid communication with the fluid channel. The fluid channel is exposed to the female adapter piece at a lateral surface of the planar structure at which the laminated layers are exposed.

35 Claims, 4 Drawing Sheets

(51) Int. Cl.
| | |
|---|---|
| *G01N 30/60* | (2006.01) |
| *B01D 15/10* | (2006.01) |
| *B01D 15/14* | (2006.01) |
| *C12M 1/12* | (2006.01) |
| *C12M 3/00* | (2006.01) |
| *F16L 13/02* | (2006.01) |
| *F16L 13/08* | (2006.01) |
| *F16L 13/10* | (2006.01) |
| *F16L 15/04* | (2006.01) |
| *F16L 47/02* | (2006.01) |
| *F16L 47/16* | (2006.01) |
| *G01N 30/16* | (2006.01) |
| *G01N 30/02* | (2006.01) |

(52) U.S. Cl.
CPC ......... *B01L 3/502715* (2013.01); *B01L 3/565* (2013.01); *C12M 23/04* (2013.01); *C12M 23/46* (2013.01); *F16L 13/0209* (2013.01); *F16L 13/08* (2013.01); *F16L 13/103* (2013.01); *F16L 15/04* (2013.01); *F16L 47/02* (2013.01); *F16L 47/16* (2013.01); *G01N 30/16* (2013.01); *G01N 30/60* (2013.01); *G01N 30/6026* (2013.01); *G01N 30/6095* (2013.01); *B01L 2200/027* (2013.01); *B01L 2200/0689* (2013.01); *G01N 2030/027* (2013.01)

(58) Field of Classification Search
USPC ................ 422/502, 501, 500, 50; 73/53.01; 435/305.1, 289.1
See application file for complete search history.

(56) References Cited

U.S. PATENT DOCUMENTS

| | | | |
|---|---|---|---|
| 6,428,053 | B1 | 8/2002 | Tai et al. |
| 6,494,500 | B1 | 12/2002 | Todosiev et al. |
| 6,926,313 | B1 | 8/2005 | Renzi |
| 2004/0141880 | A1* | 7/2004 | Handler ............ B01L 3/502715 506/15 |
| 2006/0073609 | A1* | 4/2006 | Shimizu ................. G01N 21/05 436/180 |
| 2009/0134046 | A1* | 5/2009 | Breidenthal ........ B01F 11/0045 1/45 |
| 2010/0239462 | A1 | 9/2010 | Van't Oever et al. |
| 2012/0251410 | A1 | 10/2012 | Mora-Fillat |

FOREIGN PATENT DOCUMENTS

| | | |
|---|---|---|
| EP | 1577012 A1 | 9/2005 |
| EP | 1878498 A1 | 1/2008 |
| WO | WO9825065 | 6/1998 |
| WO | WO2008106613 A2 | 9/2008 |
| WO | WO2011046615 A2 | 4/2011 |
| WO | WO2012007182 A1 | 1/2012 |

OTHER PUBLICATIONS

Machine translation of WO2012007182.
Arora, et al., "Latest Developments in Micro Total Analysis Systems", Anal. Chem. 2010, 82, 4830-4847.
International Search Report and Written Opinion dated Nov. 21, 2013 for International Application No. PCT/IB2013/051604.
Machine translation of DE102011075146.

* cited by examiner

INTEGRATED FLUIDIC CONNECTION OF PLANAR STRUCTURES FOR SAMPLE SEPARATION DEVICES

BACKGROUND ART

The present invention relates to fluidically coupling fluidic components, in particular in a high performance liquid chromatography application.

In liquid chromatography, a fluidic sample (mobile phase) may be pumped through conduits and a column comprising a material (stationary phase) which is capable of separating different components of the fluidic analyte. Such a material, so-called beads which may comprise silica gel, may be filled into a column tube which may be connected to other elements (like a sampling unit, a flow cell, containers including sample and/or buffers) by conduits.

The flow path of the mobile phase typically comprises plural individual components coupled together, which, in turn, might also be comprised of individual sub-components. Due to the high pressure applied in most HPLC applications, pressure sealing of the components in and along the flow path is required. Sealings should also provide for a small dead volume and low carryover.

A so called fitting is a fluidic component being capable of providing a sealed connection between a capillary and another fluidic conduit (such as another capillary or a channel in a substrate or the like).

U.S. Pat. No. 6,494,500 discloses a universal self-adjusting high pressure liquid connector for use with high pressure liquid chromatography (HPLC) columns requiring liquid-tight and leak free seals between fittings and unions. The apparatus provides a liquid-tight seal between the end of a HPLC end fitting and a end cap thereby eliminating any potential dead volume in the area of the connection. The apparatus comprises a body, a fixed ferrule, a replaceable ferrule, a stem disposed in the body and a biasing spring slidingly mounted on a capillary tube of that extends through the connector. The spring biases the capillary tube of the connector into the HPLC end fitting, self-adjusting and maintaining a pressure sufficient to ensure a liquid-tight seal notwithstanding the depth of the HPLC tube stop or ferrule stop of the mating HPLC column.

However, the requirements regarding sealing performance and mechanical stability of a fluidic component of fluidic measurement devices increases with further increasing operation pressure values. At the same time, fast and easy handling of such a fitting by a user is required. With the advent of planar structures with integrated fluid channels, connection technology faces new challenges.

U.S. Pat. No. 5,988,703 discloses a fluid connector system for connecting a conduit having a fluid-bearing capability to a channel having a fluid-bearing capability in a planar manifold assembly, thereby providing a substantially leak-free fluid communication between the conduit and the channel. An embodiment of the fluid connector system is effective for connecting a conduit to a planar manifold situated in a sample analysis system. The conduit is located in a fluid-handling functional device and communicates with a device port located in a port surface region on the fluid handling functional device. Located within the port surface region, and encircling the first port, is a weld projection. The channel is located in a receiver portion of a planar assembly and communicates with a manifold port. A port surface region on the exterior of the planar assembly encompasses the manifold port. The port surface regions are complementary in that they may be superimposed so as to co-locate the device port and the manifold port. The leading edge may contact the port surface region on the planar manifold in a fashion that defines a line of contact. The weld projection and the material that underlies the line of contact are both formed of electrically resistive material suited to melting and subsequent fusion via resistive heating due to a brief application of an electric current. Accordingly, upon application of a current pulse that is sufficient to cause resistive heating at the weld projection, the weld projection and the material that underlies the line of contact are heated and intermixed, thereby becoming fused together. Upon cooling, the weld projection and the line of contact are merged and thus nearly indistinguishable, thus fixing the port surface regions together such that a hermetic seal is imposed about the juncture of the superimposed device port and manifold port.

US 2010/239462 discloses an assembly comprising at least one microfluidic device and a mounting piece, this microfluidic device comprising at least one material layer and at least one first fluidic port, which first fluidic port it situated at least partially in an end surface of the material layer and which mounting piece comprises at least one fluidic component, wherein the mounting piece is coupled to the microfluidic device by means of first coupling means provided for this purpose such that the fluidic component is connected to the first fluidic port.

However, the connection of planar structures having integrated fluid channels to an environment is still difficult.

DISCLOSURE

It is an object of the invention to provide an efficiently sealing fluidic component for a fluidic device which has a planar fluidic structure.

According to an exemplary embodiment of the present invention, a fluidic device is provided which comprises a planar structure constituted by a plurality of laminated layers and accommodating one or more fluid channels extending up to a surface of the planar structure, and a female adapter piece configured for a fluid-tight accommodation of a male adapter piece having a fluid conduit, wherein the female adapter piece is connected or connectable with the planar structure so that, when the male adapter piece is accommodated in the female adapter piece, the fluid conduit is brought in fluid-tight fluid communication with the fluid channel, wherein the fluid channel is exposed to the female adapter piece at a lateral surface of the planar structure at which the laminated layers are exposed.

According to still another exemplary embodiment, a sample separation system, particularly a chromatographic separation system, for separating components of a sample fluid in a mobile phase is provided, wherein the sample separation system comprises one or more fluidic devices having the above mentioned features, a separation unit, preferably a chromatographic column, configured for separating components of the sample fluid in the mobile phase, and a fluid supply system configured to drive the sample fluid and the mobile phase to the separation unit.

According to yet another exemplary embodiment, a method of manufacturing a fluidic device is provided, wherein the method comprises laminating a plurality of layers to one another, wherein at least one of the plurality of layers is patterned to thereby form a planar structure accommodating a fluid channel extending up to a surface of the planar structure, and connecting a female adapter piece, being configured for a fluid-tight accommodation of a male adapter piece having a fluid conduit, with the planar structure so that, when the male adapter piece is accommodated in the female adapter piece, the fluid conduit is brought in fluid-tight fluid communication with the fluid channel, wherein the fluid channel is connected to the female adapter piece at a lateral surface of the planar structure at which the laminated layers are exposed.

In the context of this application, the term "fluid" may particularly denote liquids or gases, wherein optionally solid particles may be part of the fluid as well.

According to an exemplary embodiment of the invention, an integrated connection technology for the coupling of planar structures is provided. More specifically, a planar structure (such as a flat microfluidic chip) is connected to a female piece of a fitting to form a universally usable fluidic connection device. By taking this measure, and particularly by providing a fluid connection at a side surface rather than at a main surface of the microfluidic chip, the provided fluidic device allows for a basically dead volume-free connection which is capable of withstanding high pressure of several hundreds or even thousand bar or more. Therefore, a fluidic connection system can be provided which is compact, is formed of a very small number of components and is therefore easy to be operated by a user. By directly connecting the female adapter piece to an end of the fluid channel leaving the planar structure at a strip-shaped lateral surface of the layer stack (i.e. at a surface plane of the planar structure which plane includes a stacking direction of the layers), it can be ensured that the fluid flow direction at this fluidic interface is basically straight both within the planar structure and through the female piece of the fitting. With the architecture according to an embodiment of the invention, basically any desired fluid processing capability may be integrated in the planar structure for a direct fluidic connection to any desired fluidic member via the fitting, thereby providing a high degree of flexibility in the design of fluid processing systems while meeting compactness requirements.

In the following, further embodiments of the fluidic device, the sample separation system and the method will be explained.

In an embodiment, the female adapter piece is integrally fixed with the planar structure. In such an embodiment, the female adapter piece is connected to the planar structure in such a way that it is inseparable therefrom without damaging the fluidic device. By taking this measure, the number of pieces to be separately handled by a user is maintained extremely small while at the same time allowing for a safe fluid-tight connection between planar structure and female adapter piece.

In an embodiment, at least part of the laminated layers is patterned to thereby define the fluid channel. The laminated layers are connected to one another for example by adhering, bonding, soldering, etc. Each of these layers can be a planar layer so that the planar layers can be stacked on top of each to thereby form the planar structure. Before laminating, each of the layers can however be patterned by processes which are known to a skilled person as such, such as etching, lithography, etc. Superposing multiple of such patterned laminated layers allows to define fluidic channels within the planar structure, even fluidically interconnecting adjacent layers. Therefore, the fluidic channels can be formed with very small dimensions, and even complex, bifurcated fluidic networks can be constituted. Also, it is possible that processing elements (which will be described below in more detail) for fluid processing of the fluid flowing through such a fluidic network can be accommodated in the voids of the patterned layers.

In an embodiment, the fluidic device comprises a fluid processing unit located within the planar structure and configured for processing fluid flowing through the fluid channel. For example, the fluid processing unit may comprise fluid sample separation material, a chromatographic separation column, a heat exchanger, a fluidic valve, a pressure sensor, a flow rate sensor, a fluid mixer, a Polymerase Chain Reaction unit, a detector, a fluid switch, a bifurcated fluidic network, a fluid combiner, a fluid splitter, etc. A fluidic processing unit comprising fluid sample separation material such as chromatographic beads allows to perform fluidic sample separation. A chromatographic column integrated in the planar structure can either be a microscopic column, simply powder filled in the fluidic channel, or a porous body. A heat exchanger may heat the fluidic sample or may cool it. The integration of a fluidic valve in the planar structure also allows to switch between desired fluidic flow paths, thereby enabling or disabling individual ones of such flow paths. Integrating pressure sensors or flow sensors in the planar structure allows to obtain information with regard to present flow rates or pressure values of the fluid flowing through a fluidic channel, therefore allowing to regulate the system accordingly. A fluid mixer may for instance be a T-piece at which two input fluids are mixed and the mixture is output via a fluid output channel. It is also possible to provide necessary biologic, chemical and/or physical components to perform PCR. Any kind of detectors can also be integrated in the fluid processing unit. For instance, a fluorescence detector for distinguishing between different kinds of fluids or fractions in a fluidic sample may be integrated in the planar structure. A fluid switch may allow to switch between different fluidic paths, for instance to provide a predefined mixture of different fluids or to conduct a fluid along a predefined or selectable path. Also complex bifurcated fluid networks with one or more sections having more than two channels being combined in one fluidic point are possible. A fluid splitter may split an input fluid into two or more destination fluid paths.

In an embodiment, the female adapter piece is connected with the planar structure so that, when the male adapter piece is accommodated by the female adapter piece, the fluid conduit and the fluid channel are aligned along a common fluid flow direction. In other words, a fluid flowing through the fluid conduit of the planar structure and from there through the fluid channel of the female adapter piece does not have to change its flowing direction. The fluid channels may be aligned along a common linear line, at least at the fluidic connection between fluid conduit and fluid channel. Thus, the fluid flow is hardly disturbed at the fluidic interface. Undesired turbulent effects may be prevented.

In an embodiment, at least a part of the laminated layers are bonded metal layers. The metallic material of the sheets of the laminated planar structure can for instance be stainless steel, titanium, etc. By forming the planar structure from metallic sheets, not only the high pressure robustness as needed by modern biochemical applications such as liquid chromatography can be obtained, but the metallic material being also exposed at the lateral sides of the planar structure is particularly appropriate for being integrally connected to the female adapter piece, which is in many cases also made of a metallic material. For instance, in view of the metallic character of both the planar structure and the female adapter piece, they may be connected by a metal-metal connection.

In another embodiment, at least a part of the laminated layers is made of plastic material and/or ceramic material. Thus, in contrast to the previously described embodiment, it is also possible that some or all of the laminated layers are from plastic and ceramic material. Various mixtures of materials, for instance plastic and metal or ceramic and metal are possible. For example, the biocompatibility of plastic layers may be better than the biocompatibility of certain metallic materials.

In an embodiment, the fluidic device comprises a connection structure, particularly an annular connection structure, fixedly connecting the female adapter piece with the planar structure. If such a connection structure has a ring-like shape, i.e. is formed as a closed annulus, a circumferential fluid-tight sealing effect can be achieved by such a physical connection structure.

In an embodiment, the connection structure is arranged to provide for a direct physical connection between the female adapter piece and the planar structure without any other intermediate component in between. Consequently, a dead volume at this mechanical and fluidic interface can be kept extremely small. It may be particularly advantageous if a weld seam directly connects the female adapter piece and the planar structure and is formed by welding directly on the lateral surface of the planar structure. The welding (or more general formation of the connection structure) may be performed on the lateral surface, i.e. at a flange face or face side, of the planar structure so that during welding, material of at least a part of the exposed stacked layers is melted.

In an embodiment, a ratio between a smallest distance of the connection structure from the fluid channel and a smallest dimension of the fluid channel is in a range between about 1 and about 4, particularly is in a range between about 2 and about 3. This particularly holds when the connection structure is an annular welding seam surrounding the orifice outlet at which the fluidic channel leaves the planar structure at a lateral side thereof. Welding or soldering or other thermal connection techniques may involve a local heating and even melting of the planar structure in an environment of the orifice outlet which involves the risk that the fluid channel is unintentionally closed by this thermal treatment. Hence, the ratio between a smallest distance of the connection structure from the fluid channel and a smallest dimension of the fluid channel should not be too small. On the other hand, the dead volume in the connection region shall not become too large in order to avoid problems with carryover of sample material. Thus, the ratio between a smallest distance of the connection structure from the fluid channel and a smallest dimension of the fluid channel should not be too large. It has turned out that the given ranges allow to meet both requirements at the same time which is highly advantageous for the performance of the fluidic device.

In an embodiment, the connection structure comprises a weld seam, a soldering joint and/or an adhesive bond. Particularly, when the planar structure comprises metallic layers and the female adapter piece is made of a metal as well, welding or soldering are particularly appropriate connection methods. This particularly holds in the context of microfluidic devices, since correspondingly formed connection structures are capable of withstanding the high pressure conditions as being present in applications such as liquid chromatography and the like. However, alternatively, also an adhesive connection is possible, for instance for connecting plastic layers to the female adapter piece. The skilled person is certainly aware of further possibilities of connecting a lateral stack of planar layers to a female adapter piece having a reception for receiving a corresponding male piece.

In an embodiment, the female adapter piece comprises a carrier body (such as a solid cylinder or the like) being traversed by a through hole extending from a male adapter piece reception opening for receiving the male adapter piece to a planar structure connection opening, wherein the female adapter piece is connected, particularly integrally fixed, with the planar structure so that the fluid channel is exposed to the planar structure connection opening. In other words, the connection may be formed by a carrier body having a through hole via which the exposed end of the fluid channel of the planar structure is opposed to the lumen within the male adapter piece. Therefore, a very direct fluidic connection can be established, resulting in a basically dead volume-free and fluid-tight configuration.

In an embodiment, the carrier body is traversed by at least one further through hole extending from at least one further male adapter piece reception opening for receiving at least one further male adapter piece to at least one further planar structure connection opening, wherein the female adapter piece is connected, particularly integrally fixed, with the planar structure so that at least one further fluid channel of the planar structure is exposed to the at least one further planar structure connection opening. Thus, it is possible that one and the same carrier body has multiple through holes each for accommodating a separate male adapter piece to provide for a fluid connection between multiple fluid channels laterally leaving the planar structure to multiple capillaries in the male adapter pieces with only one connection body in form of the carrier body. Thus, manifold connection bodies may be constructed. For instance, a double connector or a triple connector may be formed from one piece.

In an embodiment, the connection structure is formed to be located within the through hole of the carrier body facing, particularly directly facing, the male adapter piece when accommodated in the female adapter piece to at least partially surround the planar structure connection opening. This embodiment has turned out to be highly advantageous, since it allows to form the connection by welding or the like from a fitting side rather than from a planar structure side. This may result in the formation of a high-quality sealing particularly and specifically at a position at which an open flange face of a capillary of the male adapter piece in the recess of the fitting female part abuts against the female adapter piece around the through hole and along the (particularly annular) connection structure. Hence, the welding connection may be formed specifically at the position at which the capillary abuts to a fitting surface within the recess of the female adapter piece. This contributes to the realization of a fluid-tight connection with a very small dead volume.

In an embodiment, the through hole is tapering (for instance conically or step-wise) from the male adapter piece reception opening towards the planar structure connection opening. Such a tapering through hole allows for a simple and intuitive insertion of a male adapter piece into the recess of the female adapter piece and also for a simple automatic centering of the male adapter piece within the female adapter piece.

In an embodiment, the fluidic device comprises a sealing element inserted into the through hole of the carrier body. Such a sealing element may be a sealing ring of plastic material or the like which can be interposed between the female adapter piece and the male adapter piece.

In an embodiment, the female adapter piece is configured as a needle seat of a sample injector of a sample separation apparatus and may be configured for receiving an injector needle, as which the male adapter piece may serve. In such a scenario, the fluidic device may comprise a fluid valve in fluid connection with the needle seat. The female adapter piece and the male adapter piece form a needle seat and an injector needle of an injector of a liquid chromatography apparatus. Such an injector can be configured for moving the injection needle out of the needle seat for intaking a fluidic sample through a lumen of the injector needle by sucking this fluidic sample through the lumen using a syringe pump or the like. After this, the injector needle may be driven back into the needle seat where a fluid-tight connection is established between the lumen and a connected fluidic channel within the needle seat. By reversing the previous flow direction, the fluidic sample (which may have been stored in a loop coupled to the injection needle) can then be pressed via the fluid-tight connection of the injector needle-needle seat arrangement into the fluidic channel of the needle seat and from there via the fluidic valve into a flow path between a liquid chromatography pump and a liquid chromatography column. Also in such a configuration, it may be advantageous to provide a sealed coupling between the needle seat and the planar structure (as a microfluidic chip). For the described embodiment, reference is made to DE 102011075146.

In another embodiment, the female adapter piece is configured as a fitting female piece configured for forming a fitting together with the male adapter piece configured as a fitting male piece. Thus, the two adapter pieces may together form a fitting for connecting two fluidic members.

In an embodiment, the planar structure is configured to be elastically bendable. For instance, the planar structure may be configured as a flex board which can be flexibly and elastically bent upon applying a force thereto. This opens a broad range of applications for the coupling architecture according to exemplary embodiments of the invention.

In an embodiment, the fluidic device comprises the male adapter piece being accommodated in the female adapter piece. The fluid conduit of the male adapter piece is then brought in fluid-tight high pressure-resistant fluid communication with the fluid channel.

In an embodiment, the male adapter piece comprises a capillary having the fluid conduit and having an open end with a flange face facing the fluid channel exposed at the lateral surface of the planar structure when the male adapter piece is connected to the female adapter piece. A capillary within the male adapter piece may be brought in fluid connection with the fluid channel within the planar structure by selectively inserting the male adapter piece into the female adapter piece. This allows to reduce the dead volume of the system towards zero.

In an embodiment, the male adapter piece and the female adapter piece each comprise a coupling element, wherein the coupling elements, particularly an internal thread and a cooperating external thread, are configured fora mutual coupling of the male adapter piece and the female adapter piece. In the example of the internal and external threads, a connection between female adapter piece and male adapter piece may be performed by applying a screwing operation. However, other connection techniques are possible as well, such as a snap-fit connection, a bayonet connection, etc.

In an embodiment, the fluidic device comprises at least one further female adapter piece. Each further female adapter piece may be configured for a fluid-tight accommodation of a respective one of at least one further male adapter piece each having a further fluid conduit. The one or more additional female adapter pieces are connected or connectable with the planar structure as well so that, when a respective further male adapter piece is accommodated by a respective further female adapter piece, the respective fluid conduit is brought in fluid-tight fluid communication with the fluid channel or at least one further fluid channel of the planar structure. Thus, one and the same planar structure may have multiple fluidic access openings at lateral surfaces and/or main surfaces thereof. Each of or only a part of such ends of fluidic channels within the planar structure may be connected at the respective outlet point to a corresponding female adapter piece.

In an embodiment, the connection between the planar structure and the female adapter piece is formed at a locally narrowed end of the planar structure which locally narrowed end has a width which is smaller than (for instance is at least one half or is at least one tenth of) a width of a remaining portion of the planar structure and extends at least partially into the female adapter piece. Hence, an appendix or a tip or a neck or a taper may be inserted into the reception of the female adapter piece, whereas a wider, integrally connected portion of the flat or planar structure may remain outside of the reception. Thus, the mechanical robustness of the connection may be improved and the fluidic connection between the fluid channel and the fluid conduit may be achieved with reduced gap or even without any gap in between.

In an embodiment, the connection between the planar structure and the female adapter piece is formed at a locally bent portion of the planar structure which locally bent portion extends out of a plane of a remaining portion of the planar structure. In other words, a portion of the planar structure may be bent so as to be angled with regard to a remaining portion of the planar structure. Since the planar structure may be made of metallic materials or the like, the bent portion may remain in the bent state even when a bending force is no longer applied and may keep some flexibility or adjustability. When the connection between the bent end portion and the female adapter piece is made, this flexibility helps to balance or equilibrate structural misalignments. Furthermore, bending individual portions of the planar structure may allow to adapt connection properties to user preferences.

In an embodiment, the separation unit of the sample separation apparatus is integrated in the planar structure. In other words, separation material such as chromatographic beads may be accommodated in the fluid channel of the fluidic device.

In another embodiment, the fluidic device forms part of a sample injector of the sample separation apparatus. The sample injector may be configured to introduce the sample fluid into the mobile phase, particularly via a switchable fluidic valve. In such an embodiment, the female adapter piece may serve as an injection port or needle seat and the male adapter piece may serve as an injection needle of a chromatographic sample injector.

According to embodiments of the present invention, the sample separation system further comprises at least one of a detector configured to detect separated components of the sample, a collection unit configured to collect separated components of the sample, a data processing unit configured to process data received from the liquid separation system, and a degassing apparatus for degassing the mobile phase.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment of an HPLC system comprises a pumping apparatus having a piston for reciprocation in a pump working chamber to compress liquid in the pump working chamber to a high pressure at which compressibility of the liquid becomes noticeable, and to deliver said liquid at high pressure.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (for instance from the supply), thus allowing to provide a continuous flow at the output. However, it is clear that also both pumping apparatuses might be operated in parallel (i.e. concurrently), at least during certain transitional phases for instance to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column providing the stationary phase. The column might be a glass or steel tube (for instance with a diameter from 10 µm to 10 mm and a length of 1 cm to 1 m) or a microfluidic column (as disclosed for instance in EP 1577012 A1). The individual components are retained by the stationary phase differently and separate from each other while they are propagating at different speeds through the column with the eluent. At the end of the column they elute separated, more or less one at a time. During the entire chromatographic process or during certain phases thereof the eluent might be also collected in a series of fractions. The stationary phase or adsorbent in column chromatography usually is a solid material. The most common stationary phase for column chromatography is surface modified silica gel, followed by silica gel and alumina. Cellulose powder has often been used in the past. Known are ion exchange chromatography, reversed-phase chromatography (RP), normal phase chromatography, hydrophilic interaction chromatography, size exclusion chromatography, affinity chromatography etc. The stationary phases are usually fine powders or gels whereas the particles can be partially or entirely meso- and or microporous providing extended surface area. Furthermore, there also exist monolithic columns comprising continuous porous stationary phase body for fast high performance liquid chromatography separations.

The mobile phase (or eluent) can be either a pure solvent or a mixture of different solvents. It can be chosen for instance to adjust the retention of the components of interest and/or to minimize the amount of mobile phase to run the chromatography. The mobile phase can preferably been chosen so that the different components can be separated and/or isolated effectively. The mobile phase might comprise an organic solvent like for instance methanol or acetonitrile, preferably diluted with water. For gradient operation water and organic solvent may be delivered from separate supply lines or reservoirs, from which the gradient pump delivers a programmed blend to the system. Other commonly used solvents may be isopropanol, tetrahydrofuran (THF), hexane, ethanol or other organic or inorganic liquid components and/or any combination thereof or any combination of these with aforementioned solvents or pre-mixed mixtures comprising any of the aforementioned solvents including water.

The sample fluid or sample liquid might comprise any type of process liquid, natural sample like juice, body liquids like plasma or it may be the result of a reaction like from a fermentation broth.

The fluid is preferably a liquid but may also be or comprise a gas and/or a supercritical fluid (as for instance used in supercritical fluid chromatography SFC as disclosed for instance in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
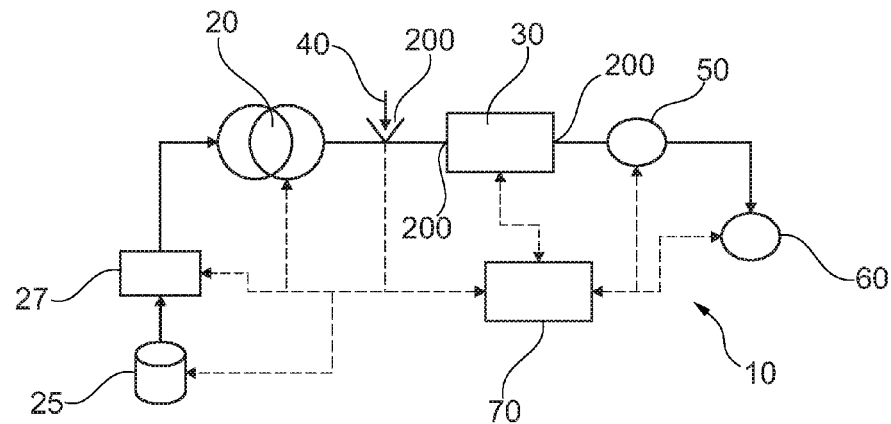
FIG. 1 shows a liquid separation device in accordance with embodiments of the present invention, particularly used in high performance liquid chromatography (HPLC).

The illustration in the drawing is schematic.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit or injector 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

From the example of FIG. 1, it can be seen that the flow path of the mobile phase typically comprises plural individual components, such as pump 20, separating device 30, sampling unit 40, and detector 50, which are coupled together and which might also be comprised of individual sub-components. Also, fluid conduits, e.g. capillaries, for conducting the fluid are provided as indicated by the solid connections in FIG. 1. Coupling of parts, components and fluid conduits, in particular when using exchangeable or modular parts, is usually provided by using fittings. Several of the individual components, particularly separating device 30 and/or injector 40, may be at least partly designed using microfluidic chips, i.e. a planar structure of laminated layers which may be internally patterned to form fluid channels and which may be equipped with fluid processing units. The mechanical and fluidic coupling of such planar structures to the environment is conventionally a challenge in terms of user convenience, sealing, carryover of historic fluids due to dead volumes and compliance with high pressure conditions. However, fluidic devices 200 according to exemplary embodiments of the invention comprising at least a planar structure and a female adapter piece may met these requirements. Just as an example, FIG. 1 schematically illustrates some exemplary positions in the liquid separation system 10 where such fluidic devices 200 may be implemented (upstream of the separation unit 30, downstream of the separation unit 30, inside the injector 40). However, they may additionally or alternatively be provided at other positions as well.

Before exemplary embodiments of such fluidic devices 200 will be described in more detail referring to the further drawings, some basic considerations of the present inventors will be summarized based on which exemplary embodiments of the invention have been derived.

In conventional connection systems for connecting planar structures to the fluidic environment, a combination of a clamping screw, a clamp fitting and the planar structure is used. This however involves a relatively high number of parts to be handled by a user, which is quite difficult from a manufacturing point of view as well as from the point of view of usability. Such systems may also be prone to leakage and may lack the mechanical stability required for high pressure liquid chromatography applications.

In view of these shortcomings, the present inventors propose to combine a planar structure to a female adapter piece at a lateral side or side edge thereof directly. Such an inline connection results in a particularly compact construction. The connection end of the planar structure can be designed in process. It is for instance possible to directly weld the planar structure to a corresponding coupling piece, i.e. the female adapter piece. Due to the weld connection of a very small number of parts (particularly a one piece solution is possible in one embodiment) a secure, fluid-tight connection can be obtained. No deterioration of the connection between fitting and planar structure due to temperature based tension loss or the like needs to be taken into account. The coupling pieces can be universally adapted depending on the requirement of a user and close the bridge between planar structures and conventional HPLC connections. The planar structure can be designed three-dimensionally in a flexible way, and the coupling pieces can be arranged in space in accordance with any user preference. It is possible to further process the flange side connection position, for instance by inserting an additional sealing structure or planar sealing area with a smaller depth of roughness. In one embodiment, it is possible to configure the female adapter piece as a needle seat of a chromatographic injector. It is possible to couple a needle seat with a capillary and a valve.

A significant advantage of exemplary embodiments is that no deformation of the fluid channel occurs as a result of the coupling with the fitting, since the forces at the connection position can be received by the fitting. The coupling piece may hence decouple the mechanical forces from the hydraulic forces.

Figure 2:
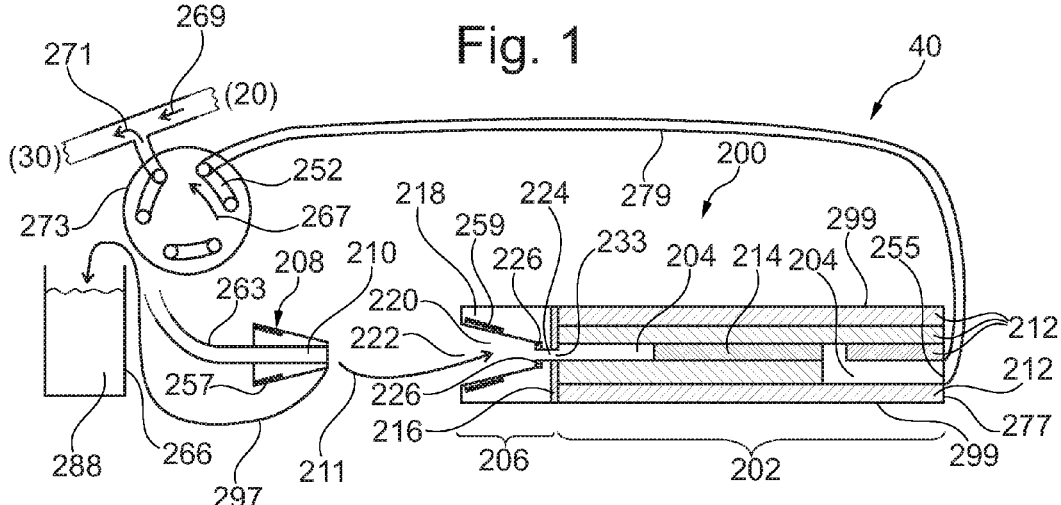
FIG. 2 schematically illustrates an injector of a liquid chromatography apparatus in which a fluidic device according to an exemplary embodiment of the invention is integrated, wherein a female adapter piece integrally connected to a planar structure forms a needle seat and a male adapter piece forms an injection needle of the injector.

FIG. 2 illustrates a detailed view of a part of an injector 40 of the liquid chromatography apparatus 10 of FIG. 1 in which a fluidic device 200 according to an exemplary embodiment is implemented.

In the present embodiment, the fluidic device 200 comprises a planar structure 202 shown in a cross-sectional view in FIG. 2. For example, the planar structure 202 may have a shape and a dimension being similar to a credit card. The planar structure 202 is constituted by a plurality of planar sheet-like metallic layers 212 which are bonded together by lamination and together form a stack. This stack has two main surfaces 299 opposing one another and being denoted as the main surface because they have the largest areas of all six surfaces of the planar structure 202. Apart from this, the planar structure 202, which can also be denoted as a microfluidic chip, comprises four lateral surfaces, two of which being parallel to the paper plane of the FIG. 2. Another lateral surface is denoted with reference numeral 277. At the lateral surfaces, the lateral ends of the individual metal layers 212 of the planar structure 202 are exposed to an environment.

In an embodiment, the thickness of the layers 212 (i.e. their extensions in the vertical direction of FIG. 2) may be in a range between 1 μm and 500 μm, particularly between 10 μm and 200 μm. The length of the laminated layer, i.e. in a horizontal direction of FIG. 2, may be in a range between 1 mm and 10 cm, more particularly between 1 cm and 5 cm. The number of the stacked layers 212 of the planar structure 202 may be in a range between 3 and 30, particularly in a range between 5 and 15.

The planar structure 202 constituted by the stacked metallic layers 212 accommodates in its interior a fluid channel 204. The fluid channel 204 is formed by void areas within the laminated layers 212 and has been formed by patterning the individual layers 212 prior to bonding them together. As can be taken from FIG. 2, the fluid channel 204 extends up to a surface of the planar structure 202 at the position which is indicated with reference numeral 255. In other words, looking onto the planar structure 202 from the right-hand side, i.e. in a direction towards the lateral surface 277, one may see the end of the fluidic channel 204 at position 255 as a void extending into the planar structure 202. As can be taken from FIG. 2, the fluid channel 204 is exposed also at opposing position 233 at the lateral surface of the planar structure 202 on the left hand side of FIG. 2 at which all the laminated layers 212 are exposed as well.

As can be taken from FIG. 2, the uppermost and the lowermost layers 212 are not patterned, i.e. are hole-free continuous layers. Also the layer directly contacting the top layer is a non-processed non-patterned continuous layer. However, the two layers in the interior of the layer stack forming the planar structure 202 are patterned so as form together the fluid channel 204. However, a fluid processing unit 214 can be integrated within this channel 204 as well. In the present embodiment, the fluid processing unit 214 may be a heat exchanger, a pressure sensor, or the like. Any desired fluid processing task may be performed by such an integrated fluid processing unit 214.

The fluidic device 200 furthermore comprises a female adapter piece 206 which is also shown in the cross-sectional view of FIG. 2. In the present embodiment, the female adapter piece 206 is permanently and inseparably connected, i.e. integrally formed with, the planar structure 202, wherein the connection is accomplished by connection layer 216 (such as a recessed layer of glue or solder). Hence, in the present embodiment, the female adapter piece 206 is integrally fixed with the planar structure 202 at the connection layer 216. The connection layer 216 is an annular layer which may cover the entire connection surface of the female adapter piece 206 which directly contacts the lateral surface of the planar structure 202. At (and optionally around) the position 233, at which a fluidic connection between the fluid channel 204 and the fluid conduit 210 occurs, no material of the connection layer 216 is present. For instance, the annular connection layer 216 can be a soldering layer.

The female adapter piece 206 is configured for a liquid-tight and pressure-tight accommodation for a correspondingly shaped and dimensioned male adapter piece 208 which is also shown in FIG. 2. The male adapter piece 208 has a fluidic conduit 210 as a lumen through which a fluid may flow. FIG. 2 furthermore shows a capillary 263 connected to and optionally extending into the male adapter piece 208. The fluid conduit 210 is to be fluidically coupled to the fluid channel 204. Hence, when the male adapter piece 208 is accommodated in an internal recess 220 of the female adapter piece 206, the fluid conduit 210 is brought in liquid-tight and pressure-tight fluid communication with the fluid channel 204. In other words, a fluid may then flow from the fluid conduit 210 through the fluid channel 204 and from there to a fluidic destination without any leakage.

As can furthermore be taken from FIG. 2, when the male adapter piece 208 is inserted into the female adapter piece 206, as indicated by reference numeral 211, the fluid conduit 210 and the fluid channel 204 are aligned along a basically horizontal direction in FIG. 2, thereby constituting a common undisturbed fluid flow direction.

As can furthermore be taken from FIG. 2, the female adapter piece 206 comprises a carrier body 218, for instance basically cylindrically shaped and made of a metallic material, being traversed by a through hole 220 extending from a male adapter piece reception opening 222 for receiving the male adapter piece 208 to a planar structure connection opening 224. The female adapter piece 206 is connected with the planar structure 202 so that the fluid channel 204 is exposed to the planar structure connection opening 224. The through hole 220 is tapering from the male adapter piece reception opening 222 towards the planar structure connection opening 224, for instance is conically tapering.

An optional sealing ring 226 which may be formed of plastic or rubber, may be inserted into the through hole 220 of the carrier body 218 so as to further promote a fluid-tight, high-pressure resistant sealing between the female adapter piece 206 and the male adapter piece 208.

Furthermore, the female adapter piece 206 may optionally comprise an internal thread 259, and the male adapter piece 208 may optionally comprise an external thread 257. The threads 259, 257 are configured to match to one another to allow for a screwing connection of the female adapter piece 206 and the male adapter piece 208, if desired.

As can be taken from FIG. 2, showing in a schematic way components of injector 40 of the liquid chromatography apparatus 10 of FIG. 1, the female adapter piece 206 is configured as a needle seat, and the male adapter piece 208 is configured as an injector needle. With the injector 40, it is possible to inject a fluidic sample 288 accommodated within a vial 266 or any other kind of fluid container into a chromatographic separation path between pump 20 and separation unit 30. For example, the male adapter piece 208 may be moved, as shown by reference numeral 297, towards and may be immersed into the fluidic sample 288 to be separated. After having intaken fluidic sample 288 through the fluid conduit 210 of the male adapter piece 208 or injection needle (for instance, but not necessarily, such fluidic sample 288 may be stored in a loop or the like), the female adapter piece 208 may be driven inside the reception of the female adapter piece 206 (see reference numeral 211), thereby establishing a fluid-tight connection with a form closure. Subsequently, the intaken sample may be injected via the fluid conduit 210 into the fluid channel 204 for further fluid processing. Since the fluid channel 204 being open at the position 255 is connected, via a tubing 279 or the like, to a fluidic valve 273, the intaken fluidic sample 288 may then be injected, by correspondingly operating the fluidic valve 273, into the fluidic path between the pump 20 and the separation unit 30, as can be taken by an arrow 271. Here it can be mixed with a mobile phase 269, such as a solvent composition. Then, a chromatographic separation may be performed. For performing such an injection, switching of the valve 252 is necessary, for instance by rotating it along a direction 267. By a corresponding rotation, ports and grooves, which are only schematically shown in FIG. 2, of the fluidic valve 273 can be brought in alignment (see reference numeral 252) so as to adjust a desired flow path.

Figure 3:
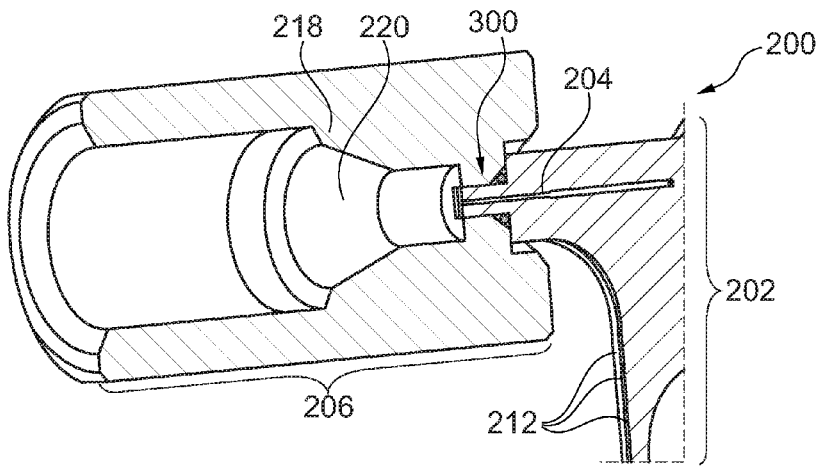
FIG. 3 shows a cross-sectional view of a fluidic device according to an exemplary embodiment of the invention.

FIG. 3 shows a three-dimensional view of fluidic device 200 according to another exemplary embodiment of the invention, in a cross-section. As can be taken from FIG. 3, the connection between the microfluidic chip or planar structure 202 on the one hand and the female adapter piece 206 on the other hand is formed at a narrow end 300 of the planar structure 202. In other words, the lateral extension of the planar structure 202 is locally reduced at the connection end thereof, at which it is fluidically and mechanically coupled to the female adapter piece 206. This simplifies the connection process and provides for a robust mechanism against an undesired connection loss between female adapter piece 206 and planar structure 202.

Figure 4:
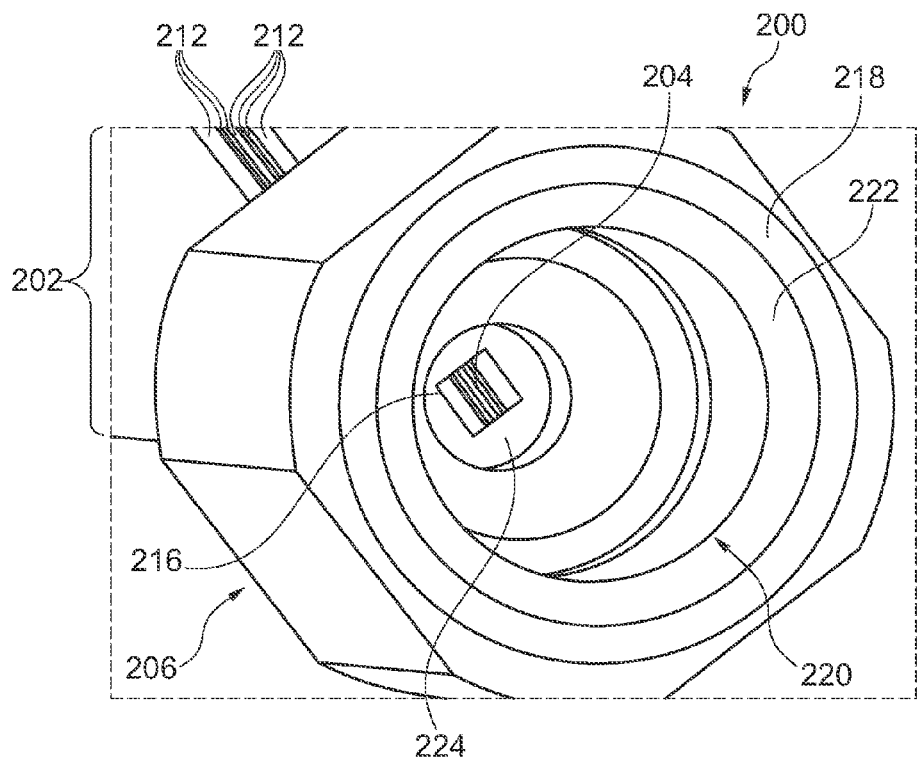
FIG. 4 shows a three-dimensional view of a fluidic device according to an exemplary embodiment of the invention.

FIG. 4 shows another three-dimensional view of a fluidic device 200 according to an exemplary embodiment of the invention. In this embodiment, an annular connection ring 216 is formed as a closed, continuously surrounding welding seam which, in the present embodiment, has a rectangular shape. By taking this measure, the sealing welding seam is formed particularly at a position at which the capillary of the male adapter piece contacts surface 224 of the female adapter piece 206. Therefore, the provision of this welding seam 216 on the side of the female adapter piece in a reception thereof rather than providing it on the opposite end thereof, allows to obtain a basically dead volume-free configuration.

Figure 5:
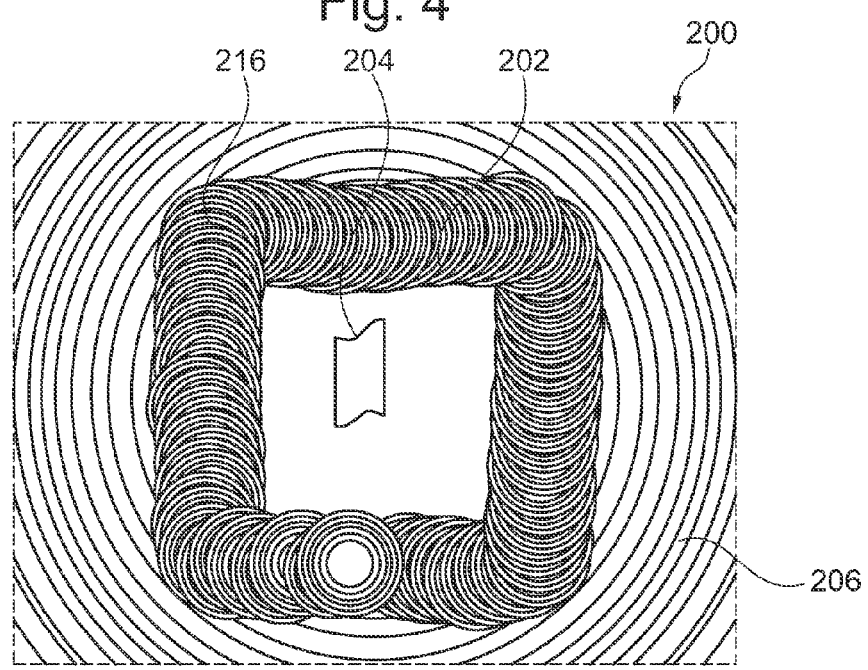
FIG. 5 is an image illustrating a fluidic device having a planar structure being welded to be permanently connected to a female adapter piece.

FIG. 5 shows an image of such a rectangular welding seam with a closed contour and also shows the exposed surface of the fluid channel 204. The welding contour is normally closed, wherein the sealing section can be post processed by machining all other means. In a finished state, the surface may be clean, and no welding marks may be visible. Alternatively to FIG. 5, the fluid channel 204 can have a round and/or centered shape.

Figure 6:
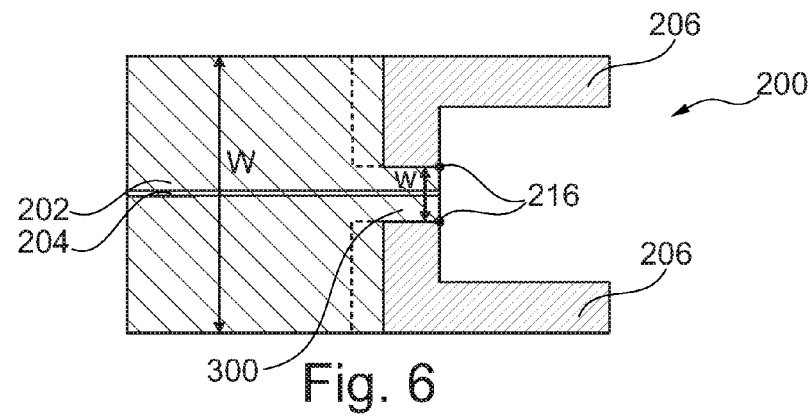
FIG. 6 shows a schematic cross-section illustrating connection of a planar structure to a female adapter piece according to an embodiment of the invention.

FIG. 6 shows a further cross-sectional view showing the fluidic and mechanical interface between planar structure 202 and female adapter piece 206. One can see two points of a circumferential connection ring 216 connecting the female adapter piece 206 to a narrow end 300 of the planar structure 202. This allows to obtain a leakage-free and dead volume-free connection.

In the embodiment of FIG. 6, the connection between the planar structure 202 and the female adapter piece 206 is formed at a locally narrowed end 300 of the planar structure 202. The locally narrowed end 300 has a width w which is significantly smaller than a width W of a remaining portion of the planar structure 202 and extends into the female adapter piece 206. Thus, the mechanical stability may be improved by introducing a form closure between the planar structure 202 and the female adapter piece 206. The locally narrowed end 300 may either completely fit into the reception of the female adapter piece 206 or may as shown with dotted lines extend beyond the reception of the female adapter piece 206 so as to leave a gap between the remaining portion of the planar structure 202 and the female adapter piece 206. The adaptor is not always welded directly on the laminated stack.

Figure 7:
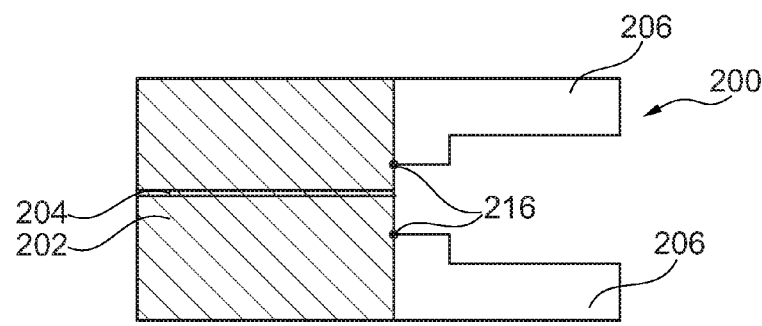
FIG. 7 shows a schematic cross-section illustrating another connection of a planar structure to a female adapter piece according to an embodiment of the invention.

In contrast to this, FIG. 7 shows the connection of a planar structure 202 having a perfect rectangular surrounding which directly connects to the female adapter piece 206 at a ring-shaped connection structure 216.

Figure 8:
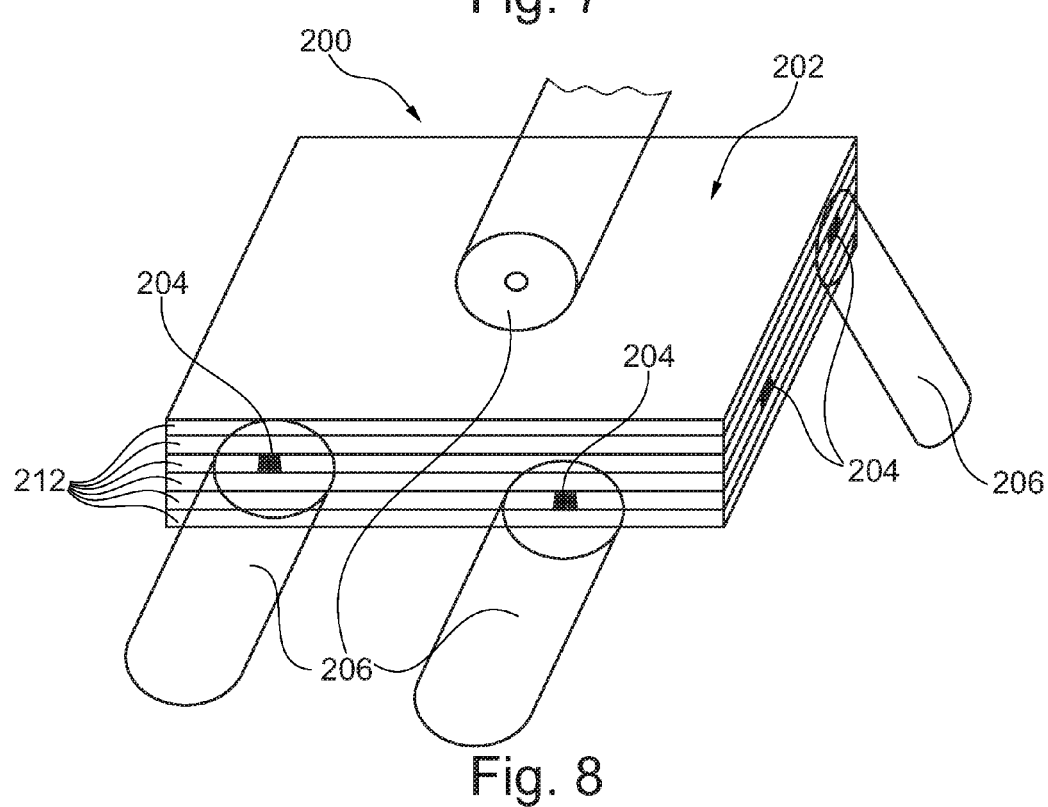
FIG. 8 shows a three-dimensional view illustrating a complex fluidic system integrated within a planar laminated structure and being connected to the environment via multiple female adapter pieces.

FIG. 8 shows a three-dimensional view of a fluidic device 200 according to yet another exemplary embodiment of the invention. As can be taken from FIG. 8, multiple fluid channels 204 are exposed at lateral sides of the laminated stack of layers 212. One of them remains exposed to the surface, whereas each of the other ones, regardless whether they are leaving the planar structure 202 at a main surface or at a lateral side surface, is connected to the environment via a female adapter piece 206, as illustrated schematically in FIG. 8. Although FIG. 8 shows the female adapter pieces 206 as individual pieces, it is possible in an alternative embodiment that they are integrated into a single surrounding piece part.

Alternatively, the planar stack may be configured and manufactured in a cylindrical outside shape and pressed into a surrounding part. After press-in of the female adapter piece function the assembly can be post machined in the outside part down to the openings of the planar structure. This results into an integrated part with internal structures and outside integrated female adapter pieces (fitting connections).

Figure 9:
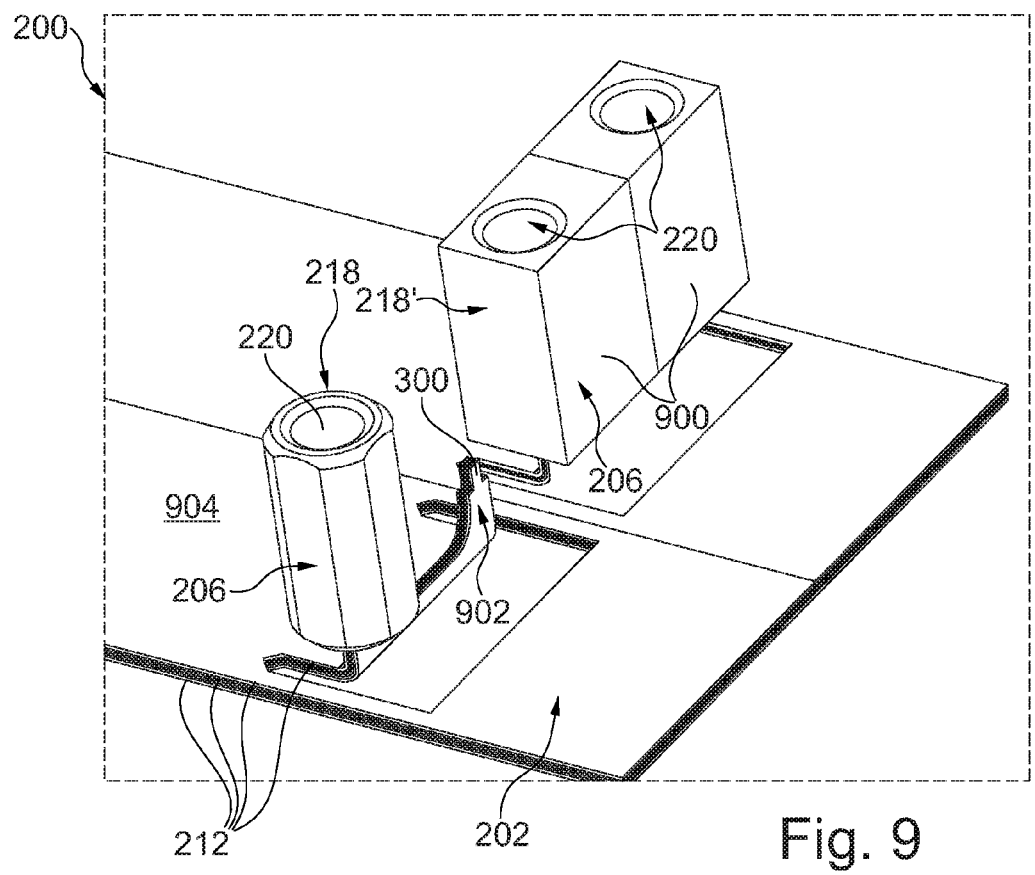
FIG. 9 shows a three-dimensional view of a fluidic device with manifold fluidic interfaces according to another exemplary embodiment of the invention.

FIG. 9 shows a three-dimensional view of a fluidic device 200 according to another exemplary embodiment of the invention having multiple fluid connections. In this embodiment, a manifold carrier body 218' is traversed by two through holes 220 extending from two male adapter piece reception openings 222—each for receiving a separate male adapter piece—to two planar structure connection openings 224 (the through holes 220 are only partially visible, compare FIG. 2 for details). The female adapter piece 206 including the manifold carrier body 218' is connected with the planar structure 202 so that two fluid channels 204 of the planar structure 202 are exposed to the planar structure connection openings 224. In the embodiment of FIG. 9, manifold carrier body 218' has two compartments 900 being fluidically uncoupled but mechanically connected.

Furthermore, the mechanical and fluidic connections between the planar structure 202 and the female adapter pieces 206 are formed at respective locally bent portions 902 of the planar structure 202 which locally bent portions 902 are bent in a curved manner by about 90° and hence extends out of a plane of a remaining portion 904 of the planar structure 202. Thus, bent portions 902 of the planar structure 202 are bent so as to be angled with regard to the remaining main portion 904 of the planar structure 202. Since the planar structure 202 is here made of metallic sheets, the bent portions 902 may remain in the bent state of FIG. 9 even when a bending force is no longer applied and may therefore maintain some flexibility or adjustability. When the connection between the bent end portions 902 and the respective female adapter pieces 206 is made, this flexibility helps to balance or equilibrate any possible structural misalignments between the components to be connected.

Figure 10:
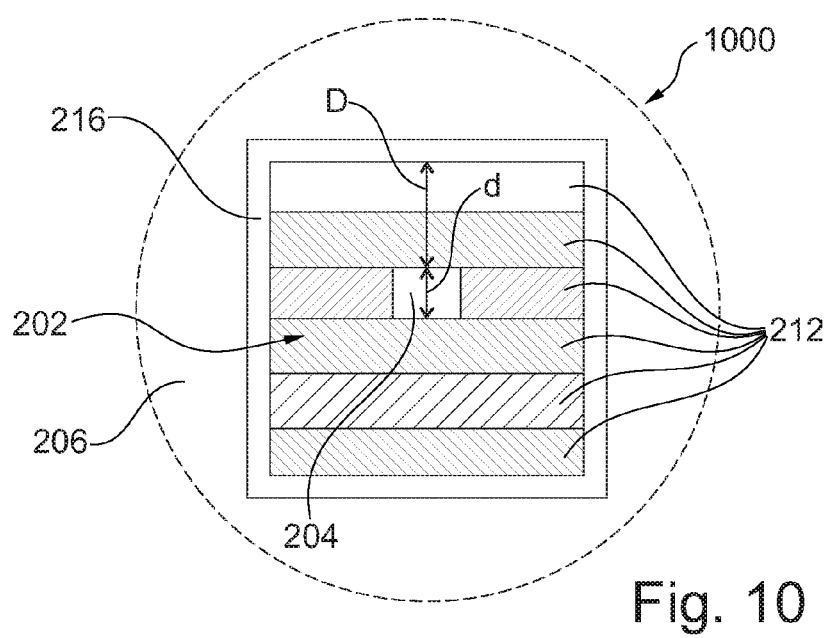
FIG. 10 shows a detail of a fluidic device according to another exemplary embodiment of the invention and illustrates a connection interface between a planar structure and a female adapter piece.

FIG. 10 shows a detail 1000 of a fluidic device according to another exemplary embodiment of the invention and illustrates a connection interface between a planar structure 202 (extending out of a paper plane of FIG. 10) and a female adapter piece 206 connected thereto.

In this embodiment, a ratio between a smallest distance D of the circumferential welding seam 216 from the fluid channel 204 and a smallest dimension d of the fluid channel 204 is about two. In FIG. 10, the connection structure 216 is formed as an annular welding seam surrounding the orifice outlet at which the fluidic channel 204 leaves the planar structure 202 at a lateral side at which the stack of laminated metal layers 212 is visible. Welding results in a local heating and even melting of the metal layers 212 around the orifice outlet. It may even happen that the fluid channel 204 is unintentionally closed during welding. To safely avoid this, the ratio between a smallest distance D of the connection structure 216 from the fluid channel 204 and a smallest dimension d of the fluid channel 204 should not be too small. On the other hand, the dead volume in the connection region shall not become too large in order to avoid problems with carryover of fluid. Thus, the ratio between the smallest distance D of the connection structure 216 from the fluid channel 204 and the smallest dimension d of the fluid channel 204 should not be too large. Selecting this ratio between 1 and 4 allows to meet both requirements at the same time.

In all embodiments, the stack of layers 212 can have main surfaces which are square shaped or basically square shaped. However, it is also possible that the main surfaces of the planar structure are strip shaped, i.e. have two different or even significantly different extensions in two orthogonal directions within the main surface.

It should be noted that the term "comprising" does not exclude other 25 elements or features and the term "a" or "an" does not exclude a plurality. Also elements described in association with different embodiments may be combined. It should also be noted that reference signs in the claims shall not be construed as limiting the scope of the claims.

The invention claimed is:

1. A fluidic device, comprising:
a planar structure comprising a plurality of laminated layers and accommodating a fluid channel extending to a lateral surface of the planar structure formed by lateral sides of the laminated layers;
a female adapter piece configured for a fluid-tight accommodation of a male adapter piece having a fluid conduit, the female adapter piece comprising a carrier body defining a through hole configured to receive the male adapter piece therein, the through hole terminating at a connection opening wherein a connection structure coupling the carrier body to the planar structure is located within the connection opening;
wherein the female adapter piece is connected or connectable with the planar structure so that, when the male adapter piece is accommodated in the female adapter piece, the fluid conduit is brought in fluid-tight fluid communication with the fluid channel within the connection opening;
wherein the fluid channel is exposed to the female adapter piece at the lateral surface of the planar structure at which the laminated layers are exposed.

2. The fluidic device according to claim 1, wherein the female adapter piece is integrally fixed with the planar structure.

3. The fluidic device according to claim 1, wherein at least part of the laminated layers is patterned to thereby define the fluid channel.

4. The fluidic device according to claim 1, comprising a fluid processing unit located within the planar structure and configured for processing fluid flowing through the fluid channel.

5. The fluidic device according to claim 4, wherein the fluid processing unit comprises at least one of the group consisting of fluid sample separation material, a chromatographic separation column, a heat exchanger, a fluidic valve, a pressure sensor, a flow rate sensor, a fluid mixer, a Polymerase Chain Reaction unit, a detector, a fluid switch, a bifurcated fluidic network, a fluid combiner, and a fluid splitter.

6. The fluidic device according to claim 1, wherein the female adapter piece is connected with the planar structure so that, when the male adapter piece is accommodated in the female adapter piece, at least a part of the fluid conduit and, at least a part of the fluid channel are aligned along a common fluid flow direction.

7. The fluidic device according to claim 1, wherein at least a part of the laminated layers are bonded metal layers.

8. The fluidic device according to claim 1, wherein at least a part of the laminated layers are made of at least one of the group consisting of a plastic material and a ceramic material.

9. The fluidic device according to claim 1, further comprising a connection structure fixedly connecting the female adapter piece with the planar structure.

10. The fluidic device according to claim 9, wherein the connection structure is arranged to provide for a direct connection between the female adapter piece and the planar structure without any other intermediate component in between.

11. The fluidic device according to claim 9, wherein a ratio between a smallest distance (D) of the connection structure from the fluid channel and a smallest dimension (d) of the fluid channel is in a range between 1 and 4.

12. The fluidic device according to claim 9, wherein the connection structure comprises at least one of a weld seam, a soldering joint and an adhesive bond.

13. The fluidic device according to claim 1, wherein the female adapter piece comprises a carrier body being traversed by a through hole extending from a male adapter piece reception opening for receiving the male adapter piece to a planar structure connection opening, wherein the female adapter piece is connected with the planar structure so that the fluid channel is exposed to the planar structure connection opening.

14. The fluidic device according to claim 9, wherein the connection structure is formed to be located within the through hole of the carrier body facing the male adapter piece when accommodated in the female adapter piece to at least partially surround the planar structure connection opening.

15. The fluidic device according to claim 13, wherein the through hole is tapering from the male adapter piece reception opening towards the planar structure connection opening.

16. The fluidic device according to claim 13, further comprising a sealing element inserted into the through hole of the carrier body.

17. The fluidic device according to claim 13, wherein the carrier body is traversed by at least one further through hole extending from at least one further male adapter piece reception opening for receiving at least one further male adapter piece to at least one further planar structure connection opening, wherein the female adapter piece is connected with the planar structure so that at least one further fluid channel of the planar structure is exposed to the at least one further planar structure connection opening.

18. The fluidic device according to claim 1, wherein the female adapter piece is configured as a needle seat configured for receiving an injector needle as the male adapter piece.

19. The fluidic device according to claim 1, wherein the female adapter piece is configured as a fitting female piece configured for forming a fitting together with the male adapter piece configured as a fitting male piece.

20. The fluidic device according to claim 1, wherein the planar structure is configured to be elastically bendable.

21. The fluidic device according to claim 1, wherein the male adapter piece comprises the fluid conduit, so that, when the male adapter piece is accommodated in the female adapter piece, the fluid conduit is brought in fluid-tight fluid communication with the fluid channel.

22. The fluidic device according to claim 21, wherein the male adapter piece is configured as an injector needle for being received in the female adapter piece being configured as a needle seat.

23. The fluidic device according to claim 22, further comprising a fluid valve in fluid communication with at least one of the injector needle and the needle seat.

24. The fluidic device according to claim 21, wherein the male adapter piece comprises a capillary enclosing the fluid conduit and having an open end with a flange face facing the fluid channel exposed at the lateral surface of the planar structure when the male adapter piece is connected to the female adapter piece.

25. The fluidic device according to claim 21, wherein the male adapter piece and the female adapter piece each comprise a coupling element, wherein the coupling elements are configured for a mutual coupling of the male adapter piece and the female adapter piece.

26. The fluidic device according to claim 1, further comprising at least one further female adapter piece each configured for a fluid-tight accommodation of a respective one of at least one further male adapter piece each having a further fluid conduit, wherein the at least one further female adapter piece is connected or connectable with the planar structure so that, when the respective further male adapter piece is accommodated in the respective further female adapter piece, the respective fluid conduit is brought in fluid-tight fluid communication with the fluid channel or at least one further fluid channel of the planar structure.

27. The fluidic device according to claim 1, wherein the connection between the planar structure and the female adapter piece is formed at a locally narrowed end of the planar structure which locally narrowed end has a width (w) which is smaller than a width (W) of a remaining portion of the planar structure and extends at least partially into the female adapter piece.

28. The fluidic device according to claim 1, wherein the connection between the planar structure and the female adapter piece is formed at a locally bent portion of the planar structure which locally bent portion extends out of a plane of a remaining portion of the planar structure.

29. A sample separation system for separating components of a sample fluid in a mobile phase, the sample separation system comprising:
   a fluidic device according to claim 1;
   a separation unit configured for separating components of the sample fluid in the mobile phase;
   a fluid supply system configured to drive the sample fluid and the mobile phase to the separation unit.

30. The sample separation system of claim 29, wherein the separation unit is integrated in the planar structure.

31. The sample separation system of claim 29, wherein the fluidic device forms part of a sample injector configured to introduce the sample fluid into the mobile phase.

32. The sample separation system of claim 29, further comprising at least one of the following features:
   the sample separation system comprises a detector configured to detect separated components of the sample fluid;
   the sample separation system comprises a collection unit configured to collect separated components of the sample fluid;
   the sample separation system comprises a data processing unit configured to process data received from the sample separation system;
   the sample separation system comprises a degassing apparatus for degassing the mobile phase.

33. A method of manufacturing a fluidic device, the method comprising:
   laminating a plurality of layers to one another, wherein at least one of the plurality of layers is patterned, to thereby form a planar structure accommodating a fluid channel extending up to a surface of the planar structure;
   connecting a female adapter piece, being configured for a fluid-tight accommodation of a male adapter piece having a fluid conduit, with the planar structure so that, when the male adapter piece is accommodated in the female adapter piece, the fluid conduit is brought in fluid-tight fluid communication with the fluid channel;
   wherein the fluid channel is connected to the female adapter piece at a lateral surface of the planar structure at which the laminated layers are exposed.

34. The method according to claim 33, wherein the connecting comprises integrally fixing the female adapter piece with the planar structure.

35. The method according to claim 33, wherein integrally fixing the female adapter piece with the planar structure comprises one of the group consisting of welding, soldering and adhering.

* * * * *